(12) United States Patent
Braddock, Jr. et al.

(10) Patent No.: US 7,811,326 B2
(45) Date of Patent: Oct. 12, 2010

(54) POSTERIOR JOINT REPLACEMENT DEVICE

(75) Inventors: Danny H. Braddock, Jr., Germantown, TN (US); Marc M. Peterman, Austin, TX (US); Scott D. Hodges, Ooltewah, TN (US); Kidong Yu, Memphis, TN (US); Steven C. Humphreys, Chattanooga, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 817 days.

(21) Appl. No.: 11/343,159

(22) Filed: Jan. 30, 2006

(65) Prior Publication Data

US 2007/0179616 A1     Aug. 2, 2007

(51) Int. Cl.
*A61F 2/44* (2006.01)
(52) U.S. Cl. .................................. 623/17.15; 623/17.14
(58) Field of Classification Search ................. 606/902, 606/246; 623/17.14–17.16
See application file for complete search history.

(56) References Cited

U.S. PATENT DOCUMENTS

| | | | |
|---|---|---|---|
| 4,349,921 A | 9/1982 | Kuntz | |
| 4,697,582 A | 10/1987 | Williams | |
| 4,697,586 A | 10/1987 | Gazale | |
| 4,702,930 A | 10/1987 | Heide et al. | |
| 4,759,769 A * | 7/1988 | Hedman et al. | 623/17.13 |
| 4,836,196 A | 6/1989 | Park et al. | |
| 4,932,975 A | 6/1990 | Main et al. | |
| 5,092,866 A | 3/1992 | Breard et al. | |
| 5,258,031 A * | 11/1993 | Salib et al. | 623/17.15 |
| 5,282,863 A | 2/1994 | Burton | |
| 5,387,213 A | 2/1995 | Breard et al. | |
| 5,401,269 A | 3/1995 | Buttner-Janz et al. | |
| 5,415,661 A | 5/1995 | Holmes | |

(Continued)

FOREIGN PATENT DOCUMENTS

DE     101 35771 A1     2/2003

(Continued)

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000648, Jun. 6, 2005, 6 pages.

(Continued)

*Primary Examiner*—Eduardo C Robert
*Assistant Examiner*—Ellen C Hammond

(57) ABSTRACT

A prosthetic device for posterior placement in an intervertebral space defined between an upper vertebrae and a lower vertebrae may include an upper articular portion configured to be at least partially disposed in the intervertebral space and a lower articular portion configured to be at least partially disposed in the intervertebral space below the upper articular portion, the upper and lower articular portions being configured to provide articulating motion to the upper and lower vertebrae. The upper and lower articular portions each may include a posterior section configured to be disposed in a location posterior of the intervertebral space. The posterior section of one of the upper and lower articular portions may include a post, and the posterior section of the other of the upper and lower articular portions may include a receiving portion configured to interact with the post during articulation.

27 Claims, 7 Drawing Sheets

U.S. PATENT DOCUMENTS

| | | | |
|---|---|---|---|
| 5,423,825 A | 6/1995 | Levine | |
| 5,443,515 A | 8/1995 | Cohen et al. | |
| 5,458,864 A | 10/1995 | Tsugeno et al. | |
| 5,507,816 A | 4/1996 | Bullivant | |
| 5,556,431 A | 9/1996 | Buttner-Janz | |
| 5,562,660 A | 10/1996 | Grob | |
| 5,562,737 A | 10/1996 | Graf | |
| 5,562,738 A | 10/1996 | Boyd et al. | |
| 5,571,109 A | 11/1996 | Bertagnoli et al. | |
| 5,607,425 A | 3/1997 | Rogozinski | |
| 5,672,175 A | 9/1997 | Martin | |
| 5,674,296 A | 10/1997 | Bryan et al. | |
| 5,676,701 A | 10/1997 | Yuan et al. | |
| 5,702,450 A | 12/1997 | Bisserie | |
| 5,728,098 A | 3/1998 | Sherman et al. | |
| 5,752,957 A | 5/1998 | Ralph et al. | |
| 5,772,661 A | 6/1998 | Michelson | |
| 5,895,428 A | 4/1999 | Berry | |
| 5,899,941 A | 5/1999 | Nishijima et al. | |
| RE36,221 E | 6/1999 | Breard et al. | |
| 5,928,284 A | 7/1999 | Mehdizadeh | |
| 5,961,516 A | 10/1999 | Graf | |
| 6,019,792 A | 2/2000 | Cauthen | |
| 6,036,088 A | 3/2000 | Itoh et al. | |
| 6,039,763 A | 3/2000 | Shelokov | |
| 6,042,582 A | 3/2000 | Ray | |
| RE36,758 E | 6/2000 | Fitz | |
| 6,106,557 A | 8/2000 | Robioneck et al. | |
| 6,113,637 A | 9/2000 | Gill et al. | |
| 6,132,464 A | 10/2000 | Martin | |
| 6,146,421 A | 11/2000 | Gordon et al. | |
| 6,156,067 A | 12/2000 | Bryan et al. | |
| 6,159,211 A | 12/2000 | Boriani et al. | |
| 6,159,214 A | 12/2000 | Michelson | |
| 6,159,244 A | 12/2000 | Suddaby | |
| 6,174,311 B1 | 1/2001 | Branch et al. | |
| 6,179,874 B1 | 1/2001 | Cauthen | |
| 6,179,875 B1 | 1/2001 | Strempel | |
| 6,190,414 B1 | 2/2001 | Young et al. | |
| 6,193,757 B1 | 2/2001 | Foley et al. | |
| 6,200,322 B1 | 3/2001 | Branch et al. | |
| 6,224,599 B1 | 5/2001 | Baynham et al. | |
| 6,224,607 B1 | 5/2001 | Michelson | |
| 6,228,118 B1 | 5/2001 | Gordon | |
| 6,231,609 B1 | 5/2001 | Mehdizadeh | |
| 6,235,059 B1 * | 5/2001 | Benezech et al. | 623/17.16 |
| 6,251,112 B1 | 6/2001 | Jackson | |
| 6,277,122 B1 | 8/2001 | McGahan et al. | |
| 6,325,827 B1 | 12/2001 | Lin | |
| 6,368,350 B1 | 4/2002 | Erickson et al. | |
| 6,402,750 B1 | 6/2002 | Atkinson et al. | |
| 6,409,766 B1 | 6/2002 | Brett | |
| 6,419,703 B1 | 7/2002 | Fallin et al. | |
| 6,419,705 B1 | 7/2002 | Erickson | |
| 6,432,140 B1 | 8/2002 | Lin | |
| 6,440,139 B2 | 8/2002 | Michelson | |
| 6,440,168 B1 | 8/2002 | Cauthen | |
| 6,454,807 B1 | 9/2002 | Jackson | |
| 6,471,724 B2 | 10/2002 | Zdeblick et al. | |
| 6,514,260 B1 | 2/2003 | Zdeblick et al. | |
| 6,517,580 B1 | 2/2003 | Ramadan et al. | |
| 6,524,312 B2 | 2/2003 | Landry et al. | |
| 6,527,804 B1 | 3/2003 | Gauchet et al. | |
| 6,540,747 B1 | 4/2003 | Marino | |
| 6,540,785 B1 | 4/2003 | Gill et al. | |
| 6,562,074 B2 | 5/2003 | Gerbec et al. | |
| 6,565,571 B1 | 5/2003 | Jackowski et al. | |
| 6,565,574 B2 | 5/2003 | Michelson | |
| 6,565,605 B2 | 5/2003 | Goble et al. | |
| 6,572,653 B1 * | 6/2003 | Simonson | 623/17.13 |
| 6,579,319 B2 | 6/2003 | Goble et al. | |
| 6,582,466 B1 | 6/2003 | Gauchet | |
| 6,582,468 B1 | 6/2003 | Gauchet | |
| 6,589,247 B2 | 7/2003 | McGahan et al. | |
| 6,599,291 B1 | 7/2003 | Foley et al. | |
| 6,610,065 B1 | 8/2003 | Branch et al. | |
| 6,610,091 B1 | 8/2003 | Reiley | |
| 6,610,093 B1 * | 8/2003 | Pisharodi | 623/17.15 |
| 6,641,582 B1 | 11/2003 | Hanson et al. | |
| 6,641,614 B1 | 11/2003 | Wagner et al. | |
| 6,648,895 B2 | 11/2003 | Burkus et al. | |
| 6,669,729 B2 | 12/2003 | Chin | |
| 6,679,915 B1 * | 1/2004 | Cauthen | 623/17.11 |
| 6,685,742 B1 * | 2/2004 | Jackson | 623/17.11 |
| 6,692,495 B1 * | 2/2004 | Zacouto | 606/247 |
| 6,699,247 B2 | 3/2004 | Zucherman et al. | |
| 6,709,458 B2 | 3/2004 | Michelson | |
| 6,733,532 B1 | 5/2004 | Gauchet et al. | |
| 6,743,255 B2 | 6/2004 | Ferree | |
| 6,749,635 B1 | 6/2004 | Bryan | |
| 6,805,714 B2 | 10/2004 | Sutcliffe | |
| 6,811,567 B2 | 11/2004 | Reiley | |
| 6,908,484 B2 | 6/2005 | Zubok et al. | |
| 6,949,123 B2 | 9/2005 | Reiley | |
| 6,984,245 B2 | 1/2006 | McGahan et al. | |
| 6,986,772 B2 | 1/2006 | Michelson | |
| 6,994,727 B2 | 2/2006 | Khandkar et al. | |
| 7,025,787 B2 | 4/2006 | Bryan et al. | |
| 7,044,971 B2 | 5/2006 | Suddaby | |
| 7,052,515 B2 | 5/2006 | Simonson | |
| 7,070,598 B2 | 7/2006 | Lim et al. | |
| 7,074,240 B2 * | 7/2006 | Pisharodi | 623/17.15 |
| 7,083,649 B2 | 8/2006 | Zucherman et al. | |
| 7,083,650 B2 | 8/2006 | Moskowitz et al. | |
| 7,090,698 B2 | 8/2006 | Goble et al. | |
| 7,137,985 B2 | 11/2006 | Jahng | |
| 7,147,665 B1 | 12/2006 | Bryan et al. | |
| 7,282,065 B2 * | 10/2007 | Kirschman | 623/17.15 |
| 7,291,150 B2 | 11/2007 | Graf | |
| 7,311,732 B2 | 12/2007 | Link et al. | |
| 7,338,525 B2 * | 3/2008 | Ferree | 623/17.11 |
| 7,338,527 B2 * | 3/2008 | Blatt et al. | 623/17.15 |
| 2001/0005796 A1 | 6/2001 | Zdeblick et al. | |
| 2001/0010021 A1 | 7/2001 | Boyd et al. | |
| 2001/0016773 A1 | 8/2001 | Serhan et al. | |
| 2001/0016774 A1 | 8/2001 | Bresina et al. | |
| 2001/0032020 A1 | 10/2001 | Besselink | |
| 2001/0034553 A1 | 10/2001 | Michelson | |
| 2001/0047207 A1 | 11/2001 | Michelson | |
| 2001/0049560 A1 | 12/2001 | Paul et al. | |
| 2002/0045943 A1 | 4/2002 | Uk | |
| 2002/0049394 A1 | 4/2002 | Roy et al. | |
| 2002/0049497 A1 | 4/2002 | Mason | |
| 2002/0052656 A1 | 5/2002 | Michelson | |
| 2002/0068976 A1 | 6/2002 | Jackson | |
| 2002/0068977 A1 | 6/2002 | Jackson | |
| 2002/0077702 A1 | 6/2002 | Castro | |
| 2002/0095154 A1 | 7/2002 | Atkinson et al. | |
| 2002/0095155 A1 | 7/2002 | Michelson | |
| 2002/0107572 A1 | 8/2002 | Foley et al. | |
| 2002/0116065 A1 | 8/2002 | Jackson | |
| 2002/0123806 A1 | 9/2002 | Reiley | |
| 2002/0128712 A1 | 9/2002 | Michelson | |
| 2002/0128713 A1 | 9/2002 | Ferree | |
| 2002/0133155 A1 | 9/2002 | Ferree | |
| 2002/0137146 A1 | 9/2002 | Choi et al. | |
| 2002/0138143 A1 | 9/2002 | Grooms et al. | |
| 2002/0143399 A1 | 10/2002 | Sutcliffe | |
| 2002/0151895 A1 | 10/2002 | Soboleski et al. | |
| 2002/0151976 A1 | 10/2002 | Foley et al. | |
| 2002/0156528 A1 | 10/2002 | Gau | |
| 2002/0161366 A1 | 10/2002 | Robie et al. | |
| 2002/0169508 A1 | 11/2002 | Songer et al. | |
| 2002/0183756 A1 | 12/2002 | Michelson | |

| | | |
|---|---|---|
| 2003/0004572 A1 | 1/2003 | Goble et al. |
| 2003/0004575 A1 | 1/2003 | Erickson |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Ferree |
| 2003/0208273 A1 | 11/2003 | Eisermann et al. |
| 2003/0233146 A1 | 12/2003 | Grinberg et al. |
| 2004/0002712 A1 | 1/2004 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1* | 2/2004 | Pisharodi .................. 623/17.15 |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |
| 2004/0073311 A1 | 4/2004 | Ferree |
| 2004/0097931 A1 | 5/2004 | Mitchell |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186570 A1 | 9/2004 | Rapp |
| 2004/0186577 A1* | 9/2004 | Ferree .................. 623/17.16 |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0243240 A1 | 12/2004 | Beaurain et al. |
| 2004/0243241 A1 | 12/2004 | Istephanous et al. |
| 2004/0249461 A1 | 12/2004 | Ferree |
| 2004/0254643 A1* | 12/2004 | Jackson .................. 623/17.11 |
| 2005/0027359 A1 | 2/2005 | Mashburn |
| 2005/0043800 A1 | 2/2005 | Paul et al. |
| 2005/0043802 A1 | 2/2005 | Eisermann et al. |
| 2005/0071008 A1 | 3/2005 | Kirschman |
| 2005/0075644 A1 | 4/2005 | DiPoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |
| 2005/0119747 A1 | 6/2005 | Monterumici et al. |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Peterman et al. |
| 2005/0154462 A1 | 7/2005 | Zucherman et al. |
| 2005/0154464 A1* | 7/2005 | Humphreys et al. ...... 623/17.16 |
| 2005/0154465 A1* | 7/2005 | Hodges et al. ........... 623/17.16 |
| 2005/0154466 A1* | 7/2005 | Humphreys et al. ...... 623/17.16 |
| 2005/0154467 A1* | 7/2005 | Peterman et al. ......... 623/17.16 |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1* | 8/2005 | Peterman et al. ......... 623/17.14 |
| 2005/0171609 A1* | 8/2005 | Humphreys et al. ...... 623/17.15 |
| 2005/0171610 A1* | 8/2005 | Humphreys et al. ...... 623/17.15 |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1* | 9/2005 | Taylor .................... 623/17.11 |
| 2005/0234551 A1 | 10/2005 | Fallin et al. |
| 2005/0234555 A1 | 10/2005 | Sutton et al. |
| 2005/0240270 A1 | 10/2005 | Zubok et al. |
| 2005/0256578 A1 | 11/2005 | Blatt et al. |
| 2005/0261773 A1 | 11/2005 | Ferree |
| 2005/0261774 A1 | 11/2005 | Trieu |
| 2005/0277930 A1 | 12/2005 | Parsons |
| 2005/0277938 A1 | 12/2005 | Parsons |
| 2005/0283237 A1 | 12/2005 | Zucherman et al. |
| 2006/0004448 A1 | 1/2006 | Casey |
| 2006/0009849 A1 | 1/2006 | Reiley |
| 2006/0036325 A1 | 2/2006 | Paul et al. |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |
| 2006/0247650 A1 | 11/2006 | Yerby et al. |
| 2007/0055378 A1 | 3/2007 | Ankney et al. |
| 2007/0179616 A1 | 8/2007 | Braddock et al. |
| 2007/0191945 A1 | 8/2007 | Yu et al. |
| 2007/0270862 A1 | 11/2007 | Yu et al. |
| 2007/0270972 A1* | 11/2007 | Gordon et al. ........... 623/17.16 |
| 2008/0027547 A1* | 1/2008 | Yu et al. .................. 623/17.13 |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| EP | 1685811 | 8/2006 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |
| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |

| | | |
|---|---|---|
| WO | WO 2004/098465 | 11/2004 |
| WO | WO2005025431 | 3/2005 |
| WO | WO2005067824 | 7/2005 |
| WO | WO2005070350 | 8/2005 |
| WO | WO2005070353 | 8/2005 |
| WO | WO 2005/112835 | 12/2005 |
| WO | WO2005117725 | 12/2005 |
| WO | WO2007087477 | 8/2007 |
| WO | WO2007124467 | 11/2007 |

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.

Patent Cooperation Treaty—European Patent Office, "Invitation to Pay Additional Fees/Communication Relating to the Results of the Partial International Search," International Application No. PCT/US2005/000586, Jun. 8, 2005, 5 pages.

Patent Cooperation Treaty—European Patent Office, "Notification of Transmittal of the International Search Report and the Written Opinion of the Internatinal Searching Authority, or the Declaration," International Application No. PCT/US2005/000585, Jun. 8, 2005, 6 pages.

Patent Cooperation Treaty—European Patent Office, "Notification of Transmittal of the International Search Report and the Written Opinion of the Internatinal Searching Authority, or the Declaration," International Application No. PCT/US2005/000704, Aug. 23, 2005, 7 pages.

Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.

European Patent Office, International Searching Authority,Notification of Transmittal of the International Search Report and the Written Opinion of the International Searching Authority or the Declaration, International Application No. PCT/US2007/060549, Feb. 10, 2007, 20 pages.

U.S. Appl. No. 11/342,961, filed Jan. 30, 2006, Yu, et al.
U.S. Appl. No. 11/393,488, filed Mar. 30, 2006, Yu, et al.
U.S. Appl. No. 11/465,541, filed Aug. 18, 2006, Yu, et al.
U.S. Appl. No. 11/494,311, filed Jul. 27, 2006, Yu, et al.

Patent Cooperation Treaty—European Patent Office, "Notification of Transmittal of the International Search Report and the Written Opinion of the International Searching Authority, or the Declaration," International Application No. PCT/US2005/00586, Oct. 1, 2005, 8 pages.

Patent Cooperation Treaty—European Patent Office, "Notification of Transmittal of the International Search Report and the Written Opinion of the International Searching Authority, or the Declaration," International Application No. PCT/US2005/000586, Dec. 16, 2005, 8 pages.

Patent Cooperation Treaty—European Patent Office, "Notification of Transmittal of the International Search Report and the Written Opinion of the International Searching Authority, or the Declaration," International Application No. PCT/US2007/060491, Apr. 25, 2007, 12 pages.

Patent Cooperation Treaty—European Patent Office, "Notification of Transmittal of the International Search Report and the Written Opinion of the International Searching Authority, or the Declaration," International Application No. PCT/US2007/074385, Dec. 19, 2007, 13 pages.

Patent Cooperation Treaty—European Patent Office, "Notification of Transmittal of the International Search Report and the Written Opinion of the International Searching Authority, or the Declaration," International Application No. PCT/US2008/065504, Mar. 3, 2009, 7 pages.

U.S. Appl. No. 11/031,602, filed Jan. 7, 2005, Humphreys et al.
U.S. Appl. No. 11/031,603, filed Jan. 7, 2005, Humphreys et al.
U.S. Appl. No. 11/031,700, filed Jan. 7, 2005, Humphreys et al.
U.S. Appl. No. 11/031,780, filed Jan. 7, 2005, Hodges et al.
U.S. Appl. No. 11/031,781, filed Jan. 7, 2005, Peterman et al.
U.S. Appl. No. 11/031,783, filed Jan. 7, 2005, Humphreys et al.
U.S. Appl. No. 11/031,903, filed Jan. 7, 2005, Humphreys et al.
U.S. Appl. No. 11/031,904, filed Jan. 7, 2005, Peterman et al.

* cited by examiner

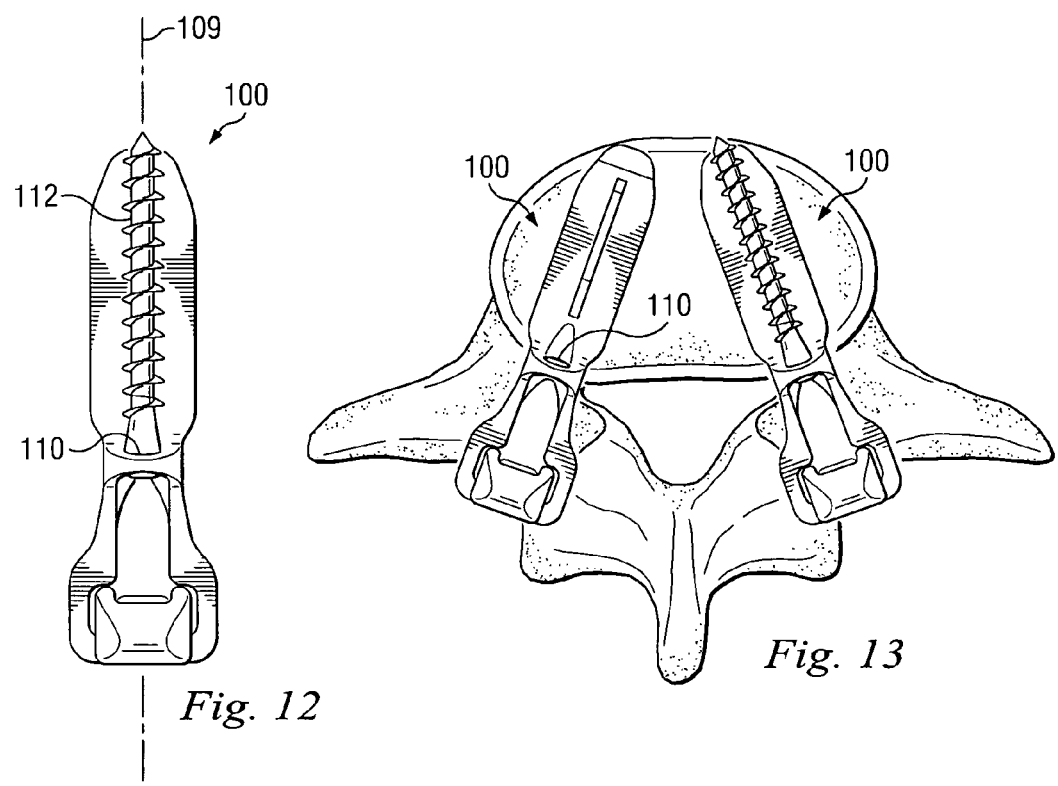
Fig. 12
Fig. 13
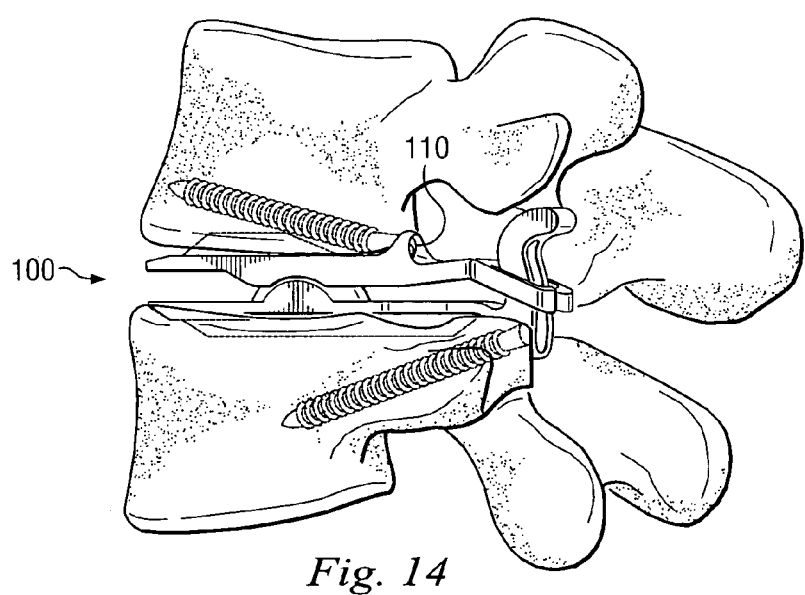
Fig. 14

POSTERIOR JOINT REPLACEMENT DEVICE

BACKGROUND

Disc arthroplasty is one way of treating injured, degraded, or diseased spinal discs. Some disc arthroplasty treatments include replacing injured discs of the joint with a motion-preserving spinal disc that allows some articulation or movement of the spinal joint. While the inserted disc may provide joint articulation to a patient, inserting the spinal disc can be an invasive and intensive procedure. For example, anterior procedures often require displacement of organs, such as the aorta and vena cava, and must be performed with great care. Further, because scar tissue may grow about the surgical site, any required second treatment can be more difficult, and may introduce additional distress to the patient.

What is needed is a prosthetic device for insertion into an intervertebral space that may be installed from a posterior position. The posterior joint replacement device disclosed herein overcomes one or more problems in the prior art.

SUMMARY OF THE INVENTION

In one exemplary aspect, this disclosure is directed to a prosthetic device for posterior placement in an intervertebral space defined between an upper vertebrae and a lower vertebrae to provide articulating motion to the upper and lower vertebrae. The device may include an upper articular portion configured to be at least partially disposed in the intervertebral space. It may also include a lower articular portion configured to be at least partially disposed in the intervertebral space below the upper articular portion. The upper and lower articular portions may be configured to provide articulating motion to the upper and lower vertebrae.

In one aspect, the upper and lower articular portions each may include a posterior section configured to be disposed in a location posterior of the intervertebral space. The posterior section of one of the upper and lower articular portions may include a post, and the posterior section of the other of the upper and lower articular portions may include a receiving portion configured to interact with the post during articulation.

In another aspect, at least one connecting hole may be associated with at least one of the upper and lower articular portions. The at least one of the upper and lower articular portions may define a longitudinal centerline and the at least one connecting hole may be aligned along the centerline.

In another exemplary aspect, this disclosure is directed toward a joint replacement device for placement in an intervertebral space defined between an upper vertebrae and a lower vertebrae to provide articulating motion to the upper and lower vertebrae. The joint replacement device may include a first joint replacement device and a second joint replacement device. The first and the second joint replacement devices each may include an upper articular device configured to be at least partially disposed in the intervertebral space and a lower articular device configured to be at least partially disposed in the intervertebral space. The upper and lower articular device may be configured to provide articulated motion to the upper and lower vertebrae. The upper and lower articular devices each may have a centerline and a screw port aligned along the centerline.

In yet another exemplary aspect, this disclosure is directed to a joint replacement device for placement in an intervertebral space defined between an upper vertebrae and a lower vertebrae to provide articulating motion to the upper and lower vertebrae. The joint replacement device may include a first joint replacement device configured to be implanted at least partially within the intervertebral disc space and a second joint replacement device configured to be implanted at least partially within the intervertebral disc space adjacent the first joint replacement device. The first and the second joint replacement devices may be substantially identical so that each can be implanted on either of a right side or the left side of the intervertebral disc space.

In some exemplary aspects, the joint replacement device disclosed herein may include one or more features disclosed in the following prior patent applications, incorporated herein in their entirety by reference:

U.S. Utility patent application Ser. No. 11/031,602, filed on Jan. 7, 2005 and entitled "Spinal Arthroplasty Device and Method;"

U.S. Utility patent application Ser. No. 11/031,603, filed on Jan. 7, 2005 and entitled "Dual Articulating Spinal Device and Method;"

U.S. Utility patent application Ser. No. 11/031,780, filed on Jan. 7, 2005 and entitled "Split Spinal Device and Method;"

U.S. Utility patent application Ser. No. 11/031,904, filed on Jan. 7, 2005 and entitled "Interconnected Spinal Device and Method;"

U.S. Utility patent application Ser. No. 11/031,700, filed on Jan. 7, 2005 and entitled "Support Structure Device and Method;"

U.S. Utility patent application Ser. No. 11/031,783, filed on Jan. 7, 2005 and entitled "Mobile Bearing Spinal Device and Method;"

U.S. Utility patent application Ser. No. 11/031,781, filed on Jan. 7, 2005 and entitled "Centrally Articulating Spinal Device and Method;" and U.S. Utility patent application Ser. No. 11/031,903, filed on Jan. 7, 2005 and entitled "Posterior Spinal Device and Method."

BRIEF DESCRIPTION OF THE DRAWINGS

FIGS. 10-12 are pictorial representations of an intervertebral prosthetic device according to another aspect.

FIGS. 13-15 are pictorial representations of the intervertebral prosthetic device of FIGS. 10-12 disposed between vertebral bodies.

DETAILED DESCRIPTION

Figure 1:
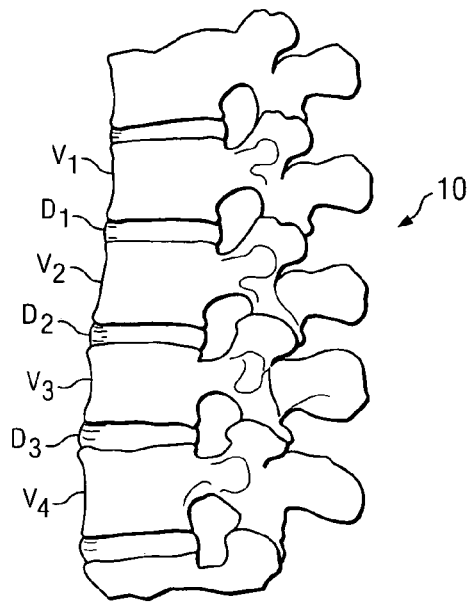
FIG. 1 is a pictorial representation of a lateral view of a portion of a vertebral column.

The present invention relates generally to vertebral reconstructive devices and, more particularly, to an intervertebral prosthetic device for implantation. For the purposes of promoting an understanding of the principles of the invention, reference will now be made to embodiments or examples illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebrae.

For the sake of further example, two of the vertebrae will be discussed with reference to FIG. 2. The two vertebrae form a spinal segment 12 including an upper vertebrae 14 and a lower vertebrae 16. Some types of disc arthroplasty require that some or all of the natural disc that would have been positioned between the two vertebrae 14, 16 be removed via a discectomy or a similar surgical procedure. Removal of the diseased or degenerated disc results in the formation of an intervertebral space S between the upper and lower vertebrae 14, 16. Although the illustration of FIG. 2 generally depicts the vertebral joint 12 as a lumbar vertebral joint, it is understood that the devices, systems, and methods of this disclosure may also be applied to all regions of the vertebral column, including the cervical and thoracic regions.

Some conventional spinal prosthetic devices are installed using an anterior procedure, requiring a physician to access the spinal column using distressing and sometimes traumatic procedures. Once a prosthetic is installed using an anterior procedure, scar tissue may build on sensitive vessels. If a second procedure is required, a physician may be required to remove the scar tissue to access the previously placed prosthetic. This sensitive procedure can cause additional distress to the patient. The intervertebral prosthetic device disclosed herein may be advantageous over prior devices because it may be installed using a posterior procedure. Accordingly, a physician need not access and disturb the critical vessels that reside at the anterior side of the spinal column. Further, if a second procedure becomes necessary, the physician has easy access to the previously placed prosthetic without removing scar tissue off of sensitive vessels. Accordingly, the procedure may be simplified and may cause less distress to the patient.

Posterior implantation procedures often include removal of facet joints or processes. Because the joints and processes operate as connection locations for ligaments and muscles, their removal may limit the ability of the joint to control the degree or range of joint articulation. Accordingly, conventional prosthetic devices implanted through a posterior procedure provide articulation, but it may be largely uncontrolled. With the removal of the muscles and ligaments, the repaired joint may become floppy. The intervertebral prosthetic devices disclosed herein limit the range of articulation, thereby providing more stability and more control to the spinal column.

Figure 3:
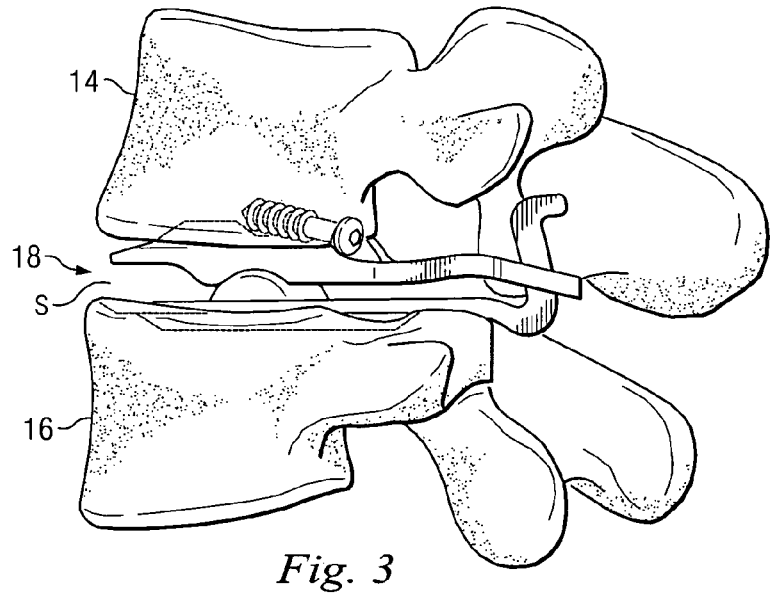
FIG. 3 is a pictorial representation of an intervertebral prosthetic device disposed between adjacent vertebral bodies.

FIG. 3 shows a side view of the vertebrae 14, 16 with an intervertebral prosthetic disc 18 in the disc space S. The disc 18 allows the vertebra 14 to articulate relative to the vertebra 16 to provide movement to the spinal joint. Sized to fit the disc space height in a manner similar to a natural intervertebral disc, such as any of discs D1-D4, the prosthetic disc 18 provides support and stabilization to the vertebrae.

Figure 4:
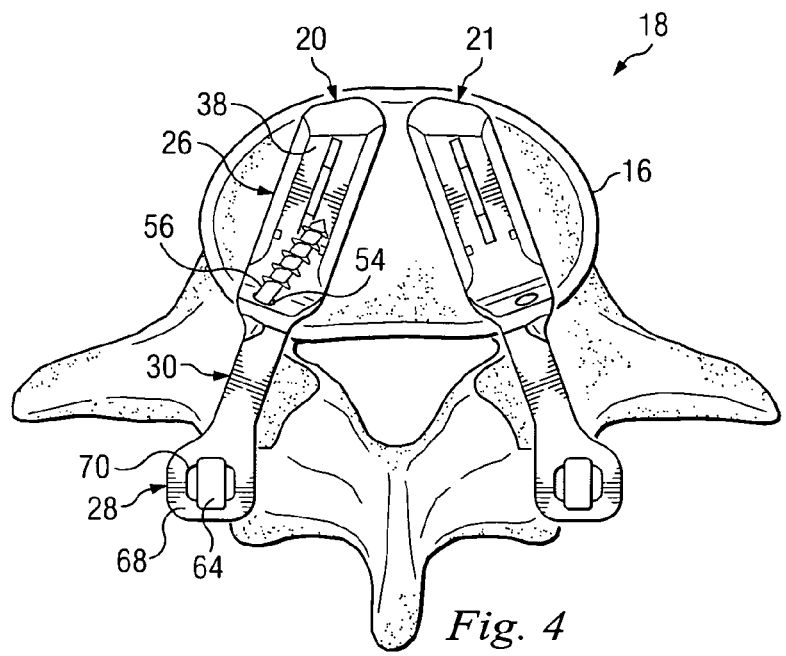
FIG. 4 is a pictorial representation of a top view of an intervertebral prosthetic device on a lower vertebral body.
Figure 5:
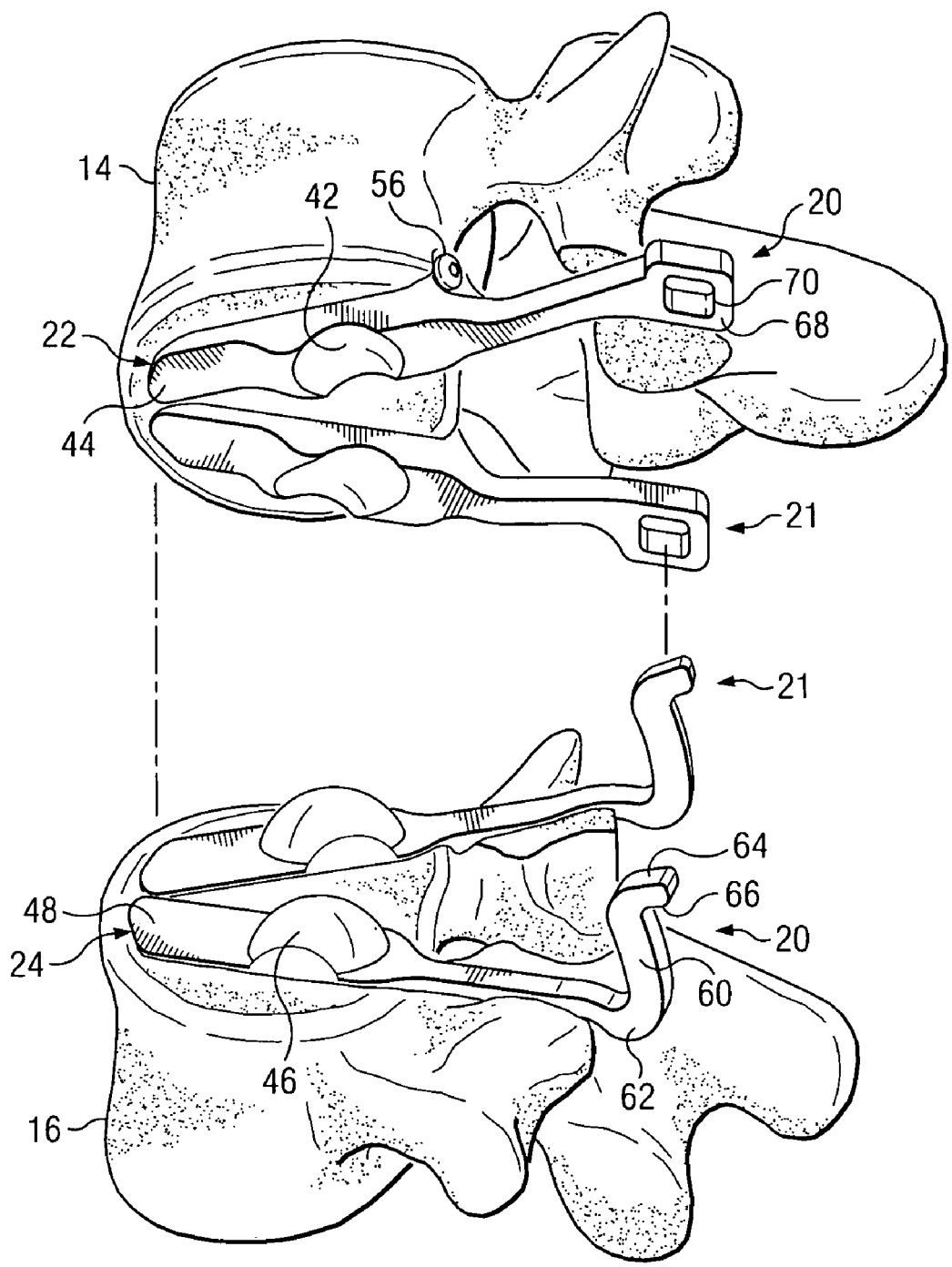
FIG. 5 is a pictorial representation showing inner features of an intervertebral prosthetic device between vertebral bodies.

FIGS. 4-8 show a number of views of at least a portion of the prosthetic disc 18. FIG. 4 shows a top view of the prosthetic disc 18 in place on the vertebra 16, and FIG. 5 shows a view of the prosthetic disc 18 in place on the vertebrae 14, 16, but with the vertebrae separated to display inner features of the prosthetic disc 18. With reference to FIG. 4, the prosthetic disc 18 may include a pair of prosthetic devices including a left prosthetic device 20 and a right prosthetic device 21 that cooperate together to take the place of the natural disc. While it is recognized that the prosthetic disc 18 may include more than one prosthetic device, the following description is primarily directed to only the left prosthetic device 20. It should be readily apparent that the right prosthetic device 21 of the prosthetic disc 18 may be substantially similar in structure and function to the left prosthetic device 20 and therefore will not be described in further detail.

With reference to FIG. 4-8, the prosthetic device 20 includes an upper articular portion 22 and a lower articular portion 24. The upper articular portion 22 includes an interdiscal section 26, a posterior section 28, and a bridge 30 extending between the interdiscal and posterior sections 26, 28. Similarly, the lower articular portion 24 includes an interdiscal section 32, a posterior section 34, and a bridge 36 extending between the interdiscal and posterior sections 32, 34.

The upper and lower articular portions 22, 24 may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various sections comprising the upper articular portion 22 and the lower articular portion 24 may be formed of different materials thus permitting metal on metal, metal on ceramic, metal on polymer, ceramic on ceramic, ceramic on polymer, or polymer on polymer constructions.

In the exemplary embodiment shown, each of the upper and lower articular portions 22, 24 are integrally formed or molded of a single piece of material. In other embodiments, one or more of the interdiscal, posterior, and bridge sections of either of the upper or lower articular portions 22, 24 may be formed separately and attached to one or more of the other sections. Attachments in these embodiments may be accomplished using any fastening mechanism known in the art including, for example, a threaded connection, a bolted connection, or a latched connection. In those embodiments, the interdiscal, posterior, and bridge sections also may be formed of different materials.

The interdiscal section 26 of the upper articular portion 22 may include a bone contacting surface 38 and an inner surface 44 opposite the bone contacting surface 38. A first articular surface 42 may form a part of the inner surface 44. In the embodiment shown, the first articular surface 42 is a recess. Similarly, the lower articular portion 24 may include a bone contacting surface 40 opposite an inner surface 48, with a second articular surface 46 forming a part of the inner surface 48 and being configured to mate with the first articular surface 42. In the embodiment shown, the second articular surface 46 is a protrusion. Together, the first and second articular surfaces 42, 46 may form an articulating joint that allows the upper and lower articular portions 22, 24 to articulate relative to each other. This articulation, in turn, may allow articulating movement of the upper vertebra 14 relative to the lower vertebra 16, and in some embodiments, may allow movement similar to that provided by a natural spinal disc. In the embodiment shown, the second articular surface 46 is a partial sphere that may rotate or translate within the first articular surface 42, forming a loosely constrained ball and socket style joint. Although shown as a ball and socket joint, the first and second articular surfaces 42, 46 may be any shape or design that allows one of the upper and lower articular portions 22, 24 to move relative to the other of the upper and lower articular portions 22, 24. For example, the first and second articular surfaces 42, 46 may include a trough and recess, a ball and saucer, or other shaped features.

As shown in FIG. 5, when implanted, the interdiscal section 26 may be situated along an inferior surface of the upper vertebra 14 and the interdiscal section 32 may be situated above a superior surface of the lower vertebra 16. However, it should be understood by one of ordinary skill in the art that the two interdiscal sections 26, 32 are not limited to such an arrangement, and may be oriented in different positions and/or shaped differently than what is illustrated herein.

The bone contacting surfaces 38, 40 of the upper and lower articular portions 22, 24 may include features or coatings which enhance the fixation of the implanted prosthetic device 20. For example, the surfaces 38, 40 may be roughened such as by chemical etching, bead-blasting, sanding, grinding, serrating, and/or diamond-cutting. All or a portion of the bone contacting surfaces 38, 40 of the upper and lower articular portions 22, 24 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

In the exemplary embodiment shown, optional upper and lower bone connectors 50, 52 are formed on the bone contacting surfaces 38, 40, respectively. These bone connectors 50, 52 extend toward the upper and lower vertebrae 14, 16 in a manner to help secure the upper and lower articular portions 22, 24 in place. In the example shown, the bone connectors 50, 52 are keels configured to extend into notches or grooves formed into the vertebral endplates. Although shown as extending along a substantial length of the upper and lower articular portions, the bone connectors 50, 52 may be of any length, either shorter or longer than that shown, and in addition, may have some other orientation or features other than that shown. For example, in some embodiments, the bone connectors are a series of ridges, protrusions, or other surface features that help fix the prosthetic device 20 in place.

In the embodiment shown, the upper articular portion 22 also includes additional features for affixing to the vertebrae 14. For example, the upper articular portion 22 includes a connecting aperture 54 (best seen in FIGS. 6 and 7) configured to receive a bone fastener 56 (shown in FIGS. 3 and 4), such as a screw. The connecting aperture 54 may be disposed adjacent a rear of the interdiscal section 26 so that the bone fastener 56 may be driven through the aperture 54 into the rear of the vertebral body of the vertebra 14. In other embodiments, the connecting aperture 54 may be disposed elsewhere so long as the bone fastener 56 in the aperture 54 may help hold the prosthetic device 20 in place. In the embodiment shown, the lower articular portion 24 does not include a connecting aperture. However, in other embodiments, one or more connecting apertures may be included.

The bridge sections 30, 36 extend rearward from the interdiscal sections 26, 32 respectively. In the embodiment shown, the bridge sections 30, 36 extend substantially along a longitudinal centerline 58 (FIG. 7) of the prosthetic device 20. In other embodiments, the bridge sections do not align with a longitudinal centerline of the interdiscal sections, but may be curved or angled to depart away from the longitudinal centerline.

The posterior sections 28, 34 may be disposed at the end of the bridge sections 30, 36 and may be configured to fit adjacent to the processes of the vertebrae 14, 16. The posterior section 34 of the lower articular portion 24 may include a post 60 having a bridge end 62 and a tail end 64. The post 60 may be configured to extend generally in a direction along the spinal column.

The bridge end 62 of the post 60 may connect to the bridge section 36. In the example shown, the bridge end 62 of the post 60 is formed by a bend in the bridge section 36, and includes a depression 65 that dips below the level of the bridge section 36. The post 60 may extend upwardly so that the tail end 64 of the post 60 may be disposed at a location higher than the bridge section 36. The tail end 64 may include a motion stop 66 configured to limit the range of articulation between the upper and lower articular portions 22, 24. In the embodiment shown, the motion stop 66 is a bend in the post 60 having a length that is configured to work together with the upper articular portion 22 to limit the available range of articular rotation of the upper and lower articular portions 22, 24. It should be noted that the post 60 may include a straight segment extending between the bridge end 62 and the tail end 64. In one exemplary embodiment, the post 60 may include a curve concentric with the curvature of the protruding articular surface 46.

Figure 6:
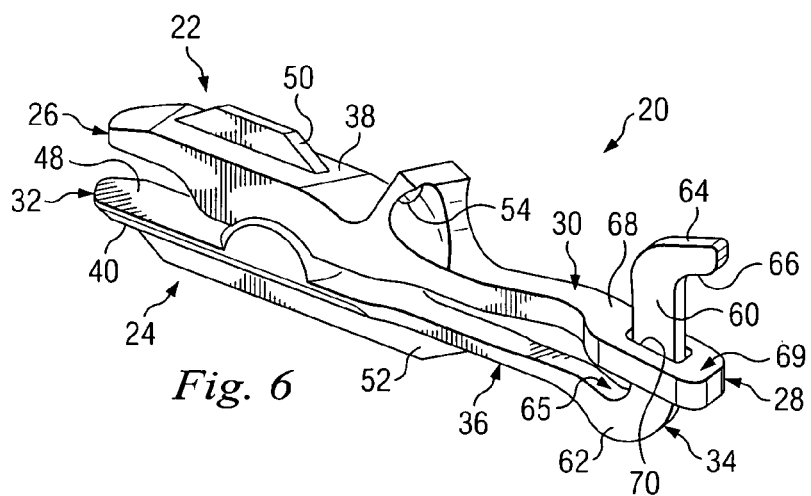
FIGS. 6, 7, and 8a-8c are pictorial representations of an intervertebral prosthetic device.

The posterior section 28 of the upper articular portion 22 includes a tab 68 having an aperture 70 formed therein that is configured to receive the post 60 of the lower articular portion 24. In the embodiment shown, the aperture 70 is a rectangular shaped hole having a width w (FIG. 7) that is less than the length of the tail end 64. A portion of the tab 68 forms a motion stop 69 that is configured to cooperate with the motion stop 66 on the post 60. Accordingly, when the upper and lower articular portions 22, 24 are assembled as shown in FIG. 6, the motion stop 66 and the motion stop 69 cooperate to limit the range of articulation of the prosthetic device 20. In addition, the aperture 70 is configured so that when the articulating surfaces 42, 46 are mated, the post 60 extends through the aperture 70 in a manner that articulation may still freely occur within the range.

Figure 2:
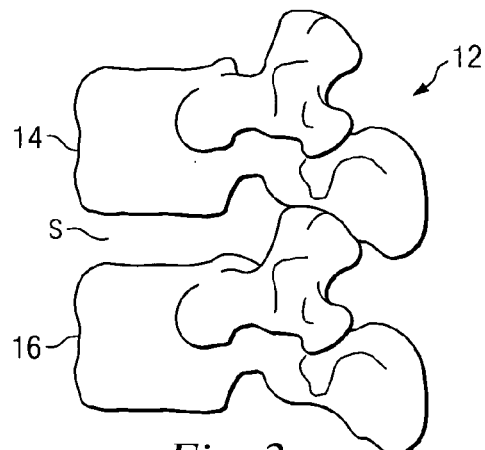
FIG. 2 is a pictorial representation of a lateral view of a pair of adjacent vertebral bodies defining an intervertebral space.

Because of the bend in the tail end 64 forming the motion stop 66, the upper and lower articular portions 22, 24 may be configured for assembly outside of the disc space S of FIG. 2. For example, the upper articular portion 22 may be placed on the lower articular portion 24 when the upper and lower articular portions 22, 24 are outside the disc space S. Further, the upper and lower articular portions 22, 24 may be difficult to disassemble within the disc space S. Therefore, the chance of the upper and lower articular portions 22, 24 becoming misaligned after implantation is virtually eliminated. Furthermore, the post 60 and aperture 70 reduce axial rotation of one of the upper and lower articular portions 22, 24 about the other of the upper and lower articular portions 22, 24. Accordingly, despite forming a ball and socket joint, the upper and lower articular portions 22, 24 are bound together so that axial rotation is limited to by the size of the aperture 70 and the post 60.

Figure 7:
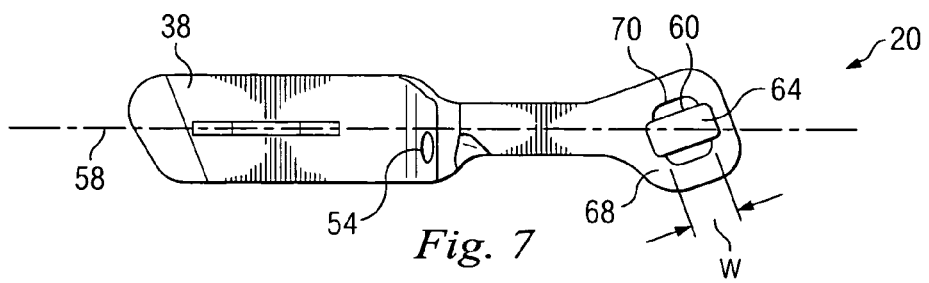

FIGS. 4 and 7 are top views of the prosthetic device 20. As apparent in these views, the post 60 and aperture 70, while still aligned along the longitudinal centerline 58, are also rotated. Accordingly, the tail end 64 is turned to point in a direction offset from the longitudinal centerline 58. Likewise, the rectangular or square aperture 70 is angled to match the angle of the tail end 64. In the embodiment shown, the angle is formed in the posterior section 34 of the lower articular portion 24, and not in the bridge section 36 of the lower articular portion 24. As seen best in FIG. 4, this angle may assist in fitting the prosthetic device 20 within the intervertebral space S by allowing the tail end to extend substantially rearward although the bridge sections and intervertebral disc sections extend into the intervertebral space S at an angle. As shown in FIG. 4, the right prosthetic device 21 includes a similar angled posterior end, but is angled in a direction opposite that of the left prosthetic device 20. In some embodiments, the posterior sections are not angled at all, while in others the bridge sections are angled or turned.

Figure 8A:
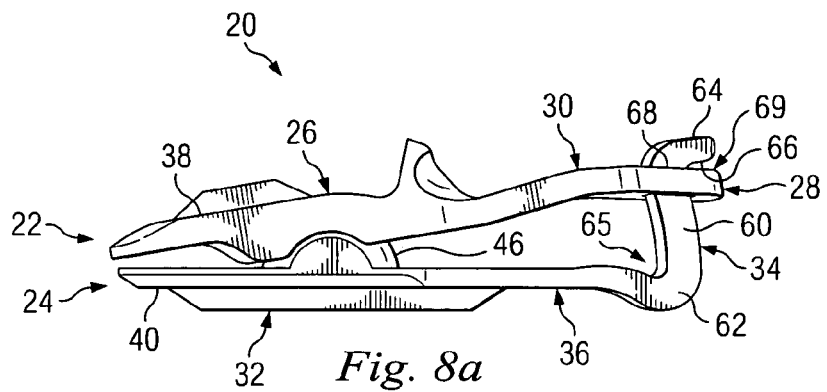
Figure 8B:
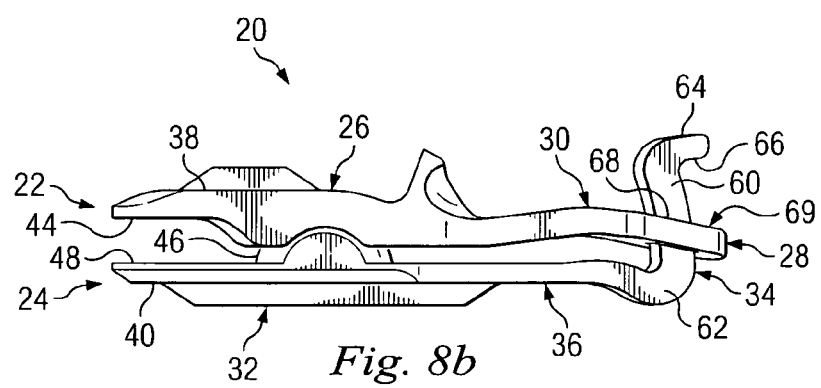
Figure 8C:
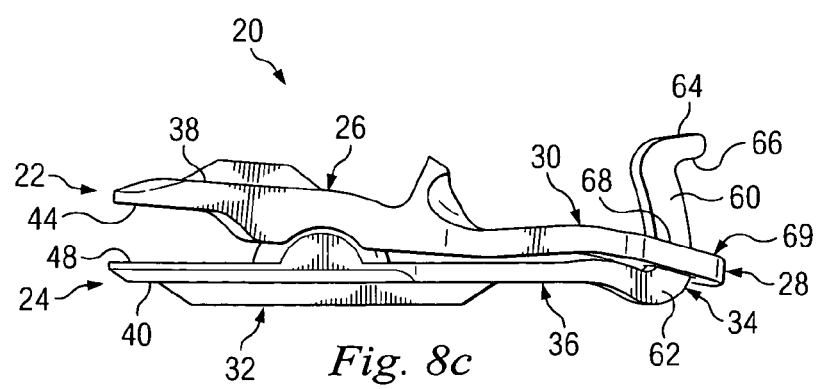

FIGS. 8a-8c show one example of an articulation range of the articulating prosthetic device 20. FIG. 8a shows the prosthetic device 20 articulated to a first limit, FIG. 8b shows the prosthetic device 20 articulated to a central position, and FIG. 8c shows the prosthetic device 20 articulated to a second limit. At the first limit in FIG. 8a, the motion stop 69 on the posterior section 34 of the upper articular portion 22 is in contact with the motion stop 66 of the lower articular portion 24. Accordingly, a flexion/extension and/or torsional articulation range of the prosthetic device 20 is limited to the amount allowed by the motion stops 66 and 69. FIG. 8b shows the prosthetic device 20 articulated to a substantially central position, with the aperture 70 being disposed about the middle region of the post 60. FIG. 8c shows the prosthetic device 20 articulated to the second limit. At the second limit, the bridge sections 30, 36 act as motion stops to limit the articulation between the upper and lower articular portions 22, 24. In the example shown, the total range of motion, represented by FIG. 8a to 8c may be about 45 degrees. However, the range of motion could be more or less than this, as controlled by the motion stops.

Figure 9:
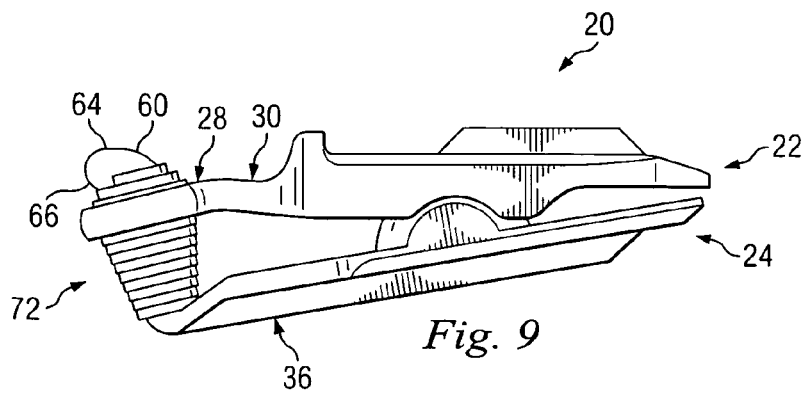
FIG. 9 is a pictorial representation of an intervertebral prosthetic device including a biasing member.
Figure 10:
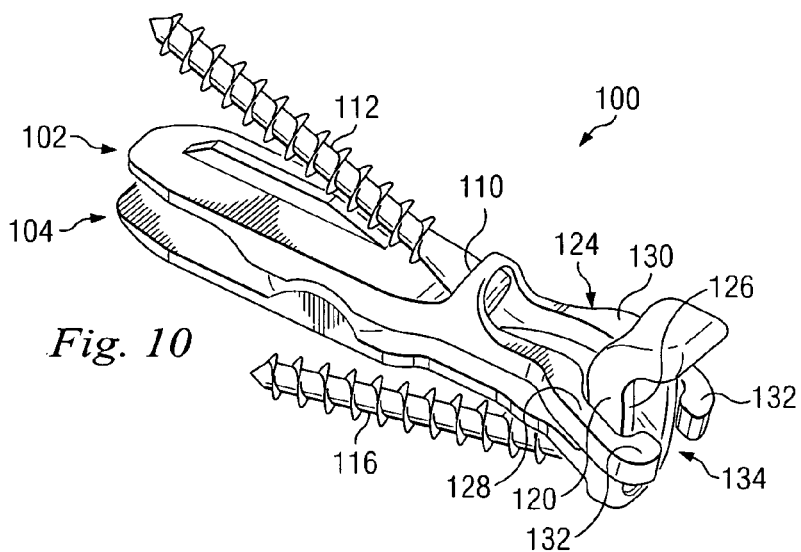

FIG. 9 shows an alternate embodiment of an articulating device. In FIG. 9, a biasing member 72 is disposed about the post 60. As discussed above, in posterior procedures, muscles and ligaments supporting the vertebrae may be disconnected from the facet joints, and the facet joints may be removed. Accordingly, implanting an articular device may allow unrestrained movement within the range of motion. To limit the undesirable ranges of motion, the biasing member 72 in FIG. 9 may bias the prosthetic device 20 to a desired position, such as a neutral position. Accordingly, although some or all the muscles and ligaments that control the articulation of a healthy spinal disc are removed, the biasing member 72 may provide a stabilizing force that controls the articular movement. In one example, the biasing member 72 is one or more springs disposed about the post 60 both above and below the posterior section 28 of the upper articular portion 22. This may provide dampening in both flexion and tension. In another embodiment, the biasing member is a elastomeric member. In yet other embodiments, the biasing member may be, for example, a friction element, an extendable band, or a bumper, such as a urethane bumper. In some embodiments, rather than being disposed both above and below the posterior section 28 of the upper articular portion 22, the biasing member 72 is disposed only above or only below the posterior section 28 of the upper articular portion 22. In other embodiments, the biasing member is disposed elsewhere, such as on the bridge sections 30, 36. In yet other embodiments, the biasing member may provide some torsional resistance to the articular device.

Another embodiment of an articular prosthetic device 100 is shown in FIGS. 10-16. The articular prosthetic device 100 may have many features similar to the articular prosthetic device 20 described above. A description of these features will not be repeated here in detail. The articular prosthetic device 100 includes an upper articular portion 102 and a lower articular portion 104, each having an interdiscal section 106, 108, respectively. The interdiscal sections 106, 108 define a longitudinal centerline 109. A first connecting aperture 110 on the upper articular portion 102 is configured to allow introduction of a bone fastener 112, such as a screw, in a direction that is substantially aligned with the longitudinal centerline 109 (FIG. 12) of the articular prosthetic device 100, so that the fastener 112 and the longitudinal centerline 109 may lie substantially within the same plane. Similarly, a second connecting aperture 114 on the lower articular portion 104 is configured to allow introduction of a bone fastener 116 in a direction that is substantially aligned with the longitudinal centerline 109 of the articular prosthetic device 100 so that the fastener 116 and the longitudinal centerline 109 may lie substantially within the same plane.

In a conventional prosthetic disc, any screws are driven into bone at an angle offset from the longitudinal centerline. As the screws are tightened, drawing the device against the bone, the device may be displaced and may move from its initial, set position. Displacement often occurs in the direction of the screw. Accordingly, if the direction of the screw is offset from the longitudinal centerline of the device, then when driven into the bone, the screw often displaces the device in a direction offset from the longitudinal centerline. This movement can create alignment discrepancies between the top and bottom articulating portions.

To assist in securing it in place, the articular prosthetic device 100 is configured so that both the first and second connecting apertures 110, 114 are configured to align the respective fasteners 112, 116 so that the longitudinal centerline 109 and the fasteners 112, 116 lie substantially within the same plane. Accordingly, when the fasteners 112, 116 draw the prosthetic device 100 tight against the bone, any movement or displacement of the prosthetic device 100 from its position is in the direction of the longitudinal centerline. Accordingly, the prosthetic device 100 may be better aligned and may sit closer to the actual desired location.

The articular prosthetic device 100 also is designed to be versatile and fit in either a right or left side of the vertebral space S. Accordingly, a physician need not determine whether the prosthetic device 100 is a left or a right device. This simplifies the surgical procedure and reduces chance of error. Further, a single prosthetic device usable for both the right and left sides may reduce and simplify manufacturing costs because only one design is required, rather than two. It should be noted, however, that the disclosed features may be included on symmetric devices, such as devices designed for use in either a left or right position, or on asymmetric devices, such as devices designed for use in one of a left and a right position.

Figure 15:
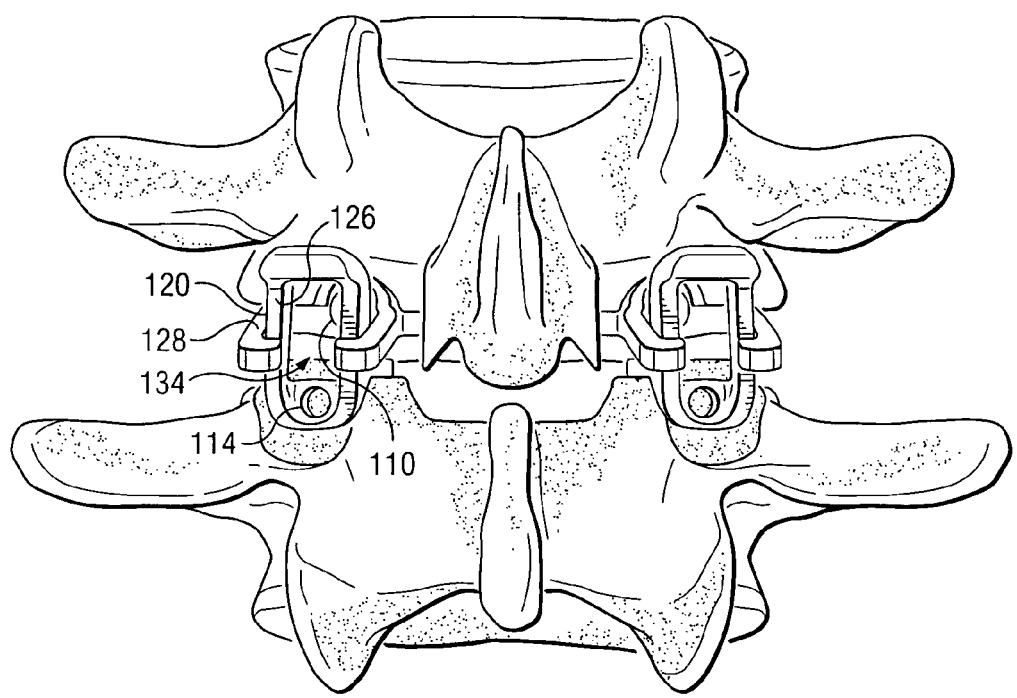
Figure 16:
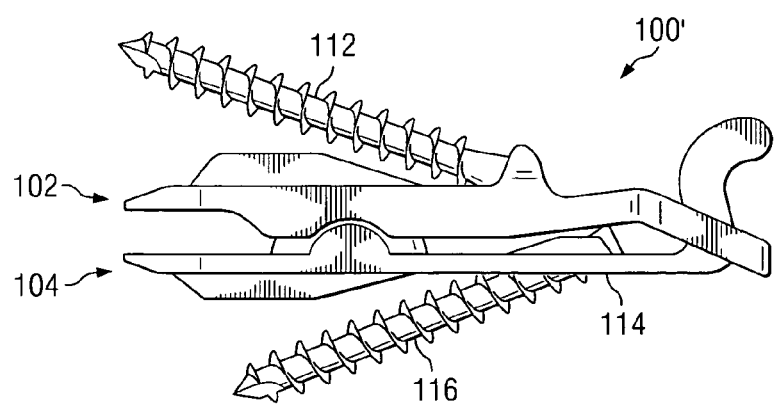
FIG. 16 is a pictorial representation of an intervertebral prosthetic device according to another aspect of the device shown in FIGS. 10-12.

Like the prosthetic device 20 described above, the prosthetic device 100 of FIGS. 10-15 includes a posterior section 118 of the lower articular portion 104 having an upwardly extending post 120. The post 120 is disposed along the centerline 109 and includes a motion stop 122 that cooperates with a posterior section 124 of the upper articular portion 102 to limit the range of articulation. In this embodiment, the post 120 includes an aperture 126 extending therethrough that provides access to the first connecting aperture 110 in the upper articular portion 102. As shown in FIG. 15, the second connecting aperture 114 is disposed in a lower portion of the post 120 and therefore can be easily accessed from the posterior side.

The posterior section 124 of the upper articular portion 102 includes a first extending arm 128 and a second extending arm 130. The arms 128, 130 extend around the post 120 so that the post is constrained from both lateral movement and from displacement along the centerline 109. Adjacent the post 120, the arms 128, 130 include motion stops 132 configured to contact the motion stop 122 on the post 120. Unlike the prosthetic device 20 described above, the arms 128, 130 of the prosthetic device 100 do not connect to form a closed aperture through which the post extends. Instead, the arms 132 with the motion stops 132 do not connect, leaving a centrally disposed gap 134. The gap 134 in the posterior section of the upper articular portion 102 of the prosthetic device 100 is aligned with the aperture 126 in the post 120 to provide access to the connecting aperture 110 of the upper articular portion 102 of the prosthetic device 100, as shown in FIG. 15.

Figure 11:
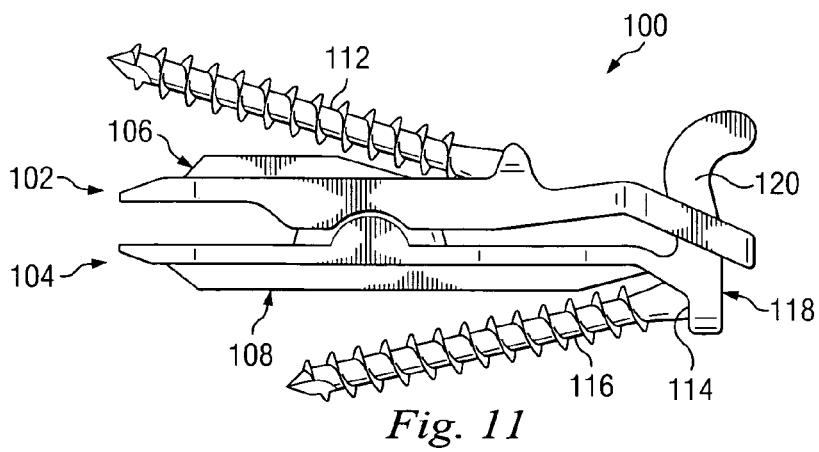

With reference to FIG. 11, the second connecting aperture 114 may be formed in the lower articular portion 104, and may be formed at the first end of the post 120. Accordingly, the first and second connecting apertures 110, 114 are not horizontally aligned, but are horizontally offset. The upper connecting aperture 110 is disposed so that the fastener 112 enters the rear of the anterior arch of the vertebra 14. The lower connecting aperture 114 is disposed so that the fastener 116 enters the pedicle and passes into the anterior arch of the lower vertebra 16. It should be noted that in other embodiments, the connecting apertures 110, 114 may horizontally aligned, and additionally, in other embodiments, the connecting aperture 114 may be disposed at any location adjacent to or between the post 120 and the articular portions. One example of this is shown with reference to an artificial intervertebral joint 100' in FIG. 16. All the features discussed with respect to the artificial intervertebral joint 100 also may be applicable to the artificial intervertebral joint 100'.

The artificial intervertebral joint 100 may be installed between the vertebrae 14, 16 as will be described below. Although installation will be described with respect to the left prosthetic device 20, it is understood that the right prosthetic device 21 may be installed in a similar manner. Further, it is understood that the prosthetic device 100 also may be installed in a similar manner. Generally, as discussed above, the artificial intervertebral prosthetic device 20 may be implanted into a body using a posterior transforaminal approach similar to the known transforaminal lumbar interbody fusion (TLIF) or posterior lumbar interbody fusion (PLIF) procedures. PLIF approaches are generally more medial and rely on more retraction of the traversing root and dura to access the vertebral interspace. TLIF approaches are typically more oblique, requiring less retraction of the exiting root, and less epidural bleeding with less retraction of the traversing structures. It is also possible to access the interspace using a far lateral approach. In some instances it is possible to access the interspace via the far lateral without resecting the facets. Furthermore, a direct lateral approach through the psoas is known. This approach avoids the posterior neural elements completely. It is anticipated that embodiments of the prosthetic devices 20, 100 could utilize any of these common approaches.

According to at least one of these approaches, an incision, such as a midline incision, may be made in the patient's back and some or all of the affected disc and surrounding tissue may be removed via the foramina. The superior endplate surface of the vertebra 14 may be milled, rasped, or otherwise resected to match the profile of the bone contacting surface 38 of the upper articular surface 22, to normalize stress distributions on the superior endplate surface of the vertebra 14, and/or to provide initial fixation prior to bone ingrowth. The preparation of the endplate of vertebra 14 may result in a flattened surface or in surface contours such as pockets, grooves, or other contours that may match corresponding features on the bone contacting surface 38. The inferior endplate of the vertebra 16 may be similarly prepared to receive the lower articular portion 24 to the extent allowed by the exiting nerve root and the dorsal root ganglia. In some procedures, the natural facet joints of vertebrae 14, 16 may be trimmed or removed to make room for the posterior component 120.

The upper and lower articular portions 22, 24 of the prosthetic device 20 may then be oriented so that the post 60 is extending through the aperture 70. Or with reference to the prosthetic device 100, so that the post 120 is extending between the two arms 128, 130. The upper and lower articular portions then may be simultaneously introduced into the transforaminal openings and are placed in the appropriate intervertebral disc space between the upper and lower vertebrae. In some procedures, because of the compact nature of the post and aperture (or post and arms), the upper and lower articular portions may be introduced through a cannula. If the pieces are modular, the prosthetic device may be implanted pieces at a time, with posterior sections of the upper and lower articular portions introduced last. The bridge sections 30, 36 may extend in a posterior direction from the interdiscal sections 26, 32 and in a posterior direction from the intervertebral disc space S. The posterior sections 28, 34 are positioned in a posterior direction of the intervertebral disc space to replace or supplement the function of the natural facet joints. Referring to the prosthetic device 20, the fastener 56 may be inserted through the connecting aperture 58 into the upper vertebra 14. Referring to the prosthetic device 100, the fastener 112 may be introduced through the gap 134 and the aperture 126 in the posterior sections, through the aperture 110, and into the upper vertebra 14. Likewise, the fastener 116 may be inserted through the connecting aperture 114 in the posterior section 118 of the lower articular portion 104 and into adjacent bone such as the pedicle of the vertebra 16.

As installed, the ball and socket type joint created by the articular surfaces 42, 46 may be relatively stable and self-centering. Both the anterior joint and the posterior connection (formed by the post and aperture connection) allow the prosthetic device 20 to resist shear forces, particularly anterior-posterior forces. Further, rotational motion about a longitudinal centerline defined by the cylindrical bodies 14, 16 may be limited both by the constraint in the post and aperture connection and by the combined constraint provided by the two prosthetic devices 20, 21.

The robust and forgiving structure of the anterior joint and the post and aperture connection permits misalignment and slight inaccuracy in the placement of the prosthetic devices 20, 21. For example, the ball and socket structure of the articular joint tolerates a certain amount of misalignment between the components. The interaction of the post and aperture may also accommodate parallel misalignment and/or anterior-posterior misalignment between the prosthetic devices 20, 21. In some embodiments, a single unilateral prosthetic device may be implanted, while in others, two devices, forming a right and a left device may be implanted. In yet other embodiments, instead of only upper and lower articulating portions that provide articulation, a three-piece articulating disc may be used. In this embodiment, a third articulating component may be disposed between the upper and lower articulating portions to provide articulation.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

We claim:

1. A prosthetic device for placement in an intervertebral space defined between an upper vertebrae and a lower vertebrae to provide articulating motion to the upper and lower vertebrae, comprising:
    an upper articular portion configured to be at least partially disposed in the intervertebral space; and
    a lower articular portion configured to be at least partially disposed in the intervertebral space below the upper articular portion, the upper and lower articular portions being configured to provide articulating motion to the upper and lower vertebrae,
    the upper and lower articular portions each including a posterior section rigidly extending from a posterior portion of the respective upper and lower articular portions in a manner to extend from a posterior portion of the intervertebral space, the posterior section being configured to be disposed in a location posterior of the intervertebral space,
    wherein the posterior section of one of the upper and lower articular portions includes a post, the post having a proximal portion and a distal portion, the distal portion of the post having a distal end including a motion stop extending in a posterior direction from a distal-most end of the distal portion of the post, the motion stop configured to cooperate with the posterior section of the other of the upper and lower articular portions to limit an articulation range of the upper and lower articular portions, and
    wherein the posterior section of the other of the upper and lower articular portions includes a receiving portion configured to interact with the post during articulation such that the post extends through the receiving portion.

2. The prosthetic device of claim 1, wherein the post is configured to extend in a direction along the spinal column.

3. The prosthetic device of claim 1, wherein the upper and lower articular portions each include:
    an interdiscal section configured to be disposed within the intervertebral space; and
    a bridge section connecting the interdiscal section to the posterior section, wherein the post is an integral extension from the bridge section of said one of the upper and lower articular portions.

4. The prosthetic device of claim 1, wherein the post includes a first end and a second end, the first end being bent to angle away from a centerline of the prosthetic device.

5. The prosthetic device of claim 1, wherein the receiving portion is an aperture, the post extending through the aperture.

6. The prosthetic device of claim 1, wherein the receiving portion is configured to extend about at least two sides of the post to limit motion of one of the upper and lower articular portions relative to the other of the upper and lower articular portions.

7. The prosthetic device of claim 1, wherein the upper and lower articular portions each include:
    an interdiscal section configured to be disposed within the intervertebral space; and
    a bridge section connecting the interdiscal section to the posterior section, wherein the bridge sections are configured to limit a range of articulating motion of the device.

8. The prosthetic device of claim 1, further comprising a biasing member associated with at least one of the upper and lower articular portions to dampen articulation of the upper articular portion relative to the lower articular portion.

9. The prosthetic device of claim 8, wherein the biasing member is disposed at the posterior end of at least one of the upper and lower articular portions.

10. The prosthetic device of claim 8, wherein the biasing member is configured to resist motion of the post relative to the receiving member.

11. The prosthetic device of claim 8, wherein the biasing member is configured to dampen motion in both flexion and extension.

12. The prosthetic device of claim 8, wherein the biasing member is at least one of a spring, an elastomeric ring, a high-friction element, and a band.

13. The prosthetic device of claim 8, wherein the resistance member is disposed about the post.

14. The prosthetic device of claim 1, further comprising at least one fastener configured to attach at least one of the upper and lower articular portions to at least one of the upper and lower vertebrae.

15. The prosthetic device of claim 14, wherein the fasteners are screws substantially aligned along a centerline.

16. The prosthetic device of claim 1, further comprising a connecting hole formed in at least one of the upper and lower articular portions.

17. The prosthetic device of claim 16, wherein the connecting hole is aligned with a centerline of the at least one of the upper and lower articular portions.

18. The prosthetic device of claim 1, wherein the post includes an aperture formed therein for passage of a fastener.

19. The joint replacement device of claim 1, wherein the receiving portion comprises a through hole.

20. The joint replacement device of claim 1, wherein the post is integrally formed with the posterior section.

21. The joint replacement device of claim 20, wherein the posterior is integrally formed with said one of the upper and lower articular portions.

22. The joint replacement device of claim 1, wherein the posterior section includes a connecting aperture configured to receive a bone fastener.

23. The joint replacement device of claim 22, further comprising a bone fastener configured for insertion through the connecting aperture.

24. The joint replacement device of claim 22, wherein the connecting aperture is offset from a centerline through the articular portions and posterior portions.

25. The joint replacement device of claim 1, wherein the post extends posteriorly at an angle oblique to a longitudinal axis of the device.

26. A joint replacement device for placement in an intervertebral space defined between an upper vertebrae and a lower vertebrae to provide articulating motion to the upper and lower vertebrae, comprising:
- a first joint replacement device configured to be implanted at least partially within the intervertebral disc space;
- a second joint replacement device configured to be implanted at least partially within the intervertebral disc space adjacent the first joint replacement device,
- wherein the first and the second joint replacement devices are substantially identical so that each can be implanted on either of a right side or a left side of the intervertebral disc space,
- wherein the first and the second joint replacement devices each include:
  - an upper articular portion having an interdiscal section and a posterior section, the interdiscal section configured to be at least partially disposed in the intervertebral space and the posterior section configured to be disposed in a location posterior of the respective upper or lower vertebrae, the posterior section rigidly extending from a posterior portion of the upper articular portion in a manner to extend from a posterior portion of the intervertebral space;
  - a lower articular portion having an interdiscal section and a posterior section, the interdiscal section configured to be at least partially disposed in the intervertebral space and the posterior section configured to be disposed in a location posterior of the respective upper or lower vertebrae,
  - the upper and lower articular portions being configured to provide articulated motion to the upper and lower vertebrae,
- wherein the posterior section of one of the upper and lower articular portions includes a post, the post having a proximal portion and a distal portion, the distal portion of the post having a distal end including a motion stop extending in a posterior direction from a distal-most end of the distal portion of the post, the motion stop configured to cooperate with the posterior section of the other of the upper and lower articular portions to limit an articulation range of the upper and lower articular portions, and
- wherein the posterior section of the other of the upper and lower articular portions includes a receiving portion configured to interact with the post during articulation such that the posts extends through the receiving portion.

27. The joint replacement device of claim 26, wherein the upper and lower articular devices each have a centerline and a screw port aligned along the centerline.

* * * * *